(12) United States Patent
Hakky et al.

(10) Patent No.: US 6,171,230 B1
(45) Date of Patent: Jan. 9, 2001

(54) FEMALE INCONTINENCE CATHETER

(75) Inventors: Said I. Hakky; A-Hamid Hakki, both of Largo, FL (US)

(73) Assignee: Canox International Ltd., Largo, FL (US)

( * ) Notice: Under 35 U.S.C. 154(b), the term of this patent shall be extended for 0 days.

(21) Appl. No.: 09/262,606

(22) Filed: Mar. 4, 1999

(51) Int. Cl.⁷ .................................................... A61F 2/00
(52) U.S. Cl. ................................................ 600/29; 600/31
(58) Field of Search ................................ 600/29, 30, 31

(56) References Cited

U.S. PATENT DOCUMENTS 5,114,398 * 5/1992 Trick et al. ............................ 600/29
5,713,829 * 2/1998 Hakky et al. .......................... 600/29
5,749,826 * 5/1998 Faulkner ............................... 600/29

* cited by examiner

*Primary Examiner*—Max Hindenburg
*Assistant Examiner*—Brian Szmal
(74) *Attorney, Agent, or Firm*—Rosenberg, Klein & Lee (57) ABSTRACT

A female incontinence device made of a soft semi-collapsed hollow tube that can be easily inserted into the bladder by a patient or a healthcare professional. The proximal end can open diagonally within the bladder to retain the catheter in the proper position, and can be easily removed without the use of special tools. A valve system which is pressure-sensitive is provided at the distal end such that it can be manually activated to empty the bladder.

20 Claims, 10 Drawing Sheets

FEMALE INCONTINENCE CATHETER

BACKGROUND OF THE INVENTION

1. Field of the Invention

This invention relates generally to the field of surgical devices and, more particularly, to a female intraurethral incontinence device which consists of a soft indwelling semi-collapsed catheter for alleviating female urinary incontinence.

2. Discussion of the Prior Art

The female urethra is approximately two inches long. It is situated between the labia and at the entrance of the vaginal tract. It is anatomically difficult or impossible to place an external device on the urethra if the female patient is incontinent. Therefore, incontinent female patients generally employ absorbent devices, such as sanitary towels or pads to compensate for this problem. Recently, suction pads or continence shields have become available in the marketplace. These are essentially suction devices which can be applied externally onto the female urethra in selected patients. One example of this type of device is marketed by Bard Urological Inc., of Georgia under the trade name CAPSURE. Such devices are at best used in highly selected patients, and must be changed many times daily. In addition, it is often difficult to produce an adequate vacuum to hold the device in the proper position onto the user's body for the device to sufficiently function. Another example of this type of device is taught in U.S. Pat. No. 5,813,973. The use of jelly for application of this type of device also tends to irritate the urethra, thus producing urethritis or infection.

An indwelling female catheter will have a broader application, and will not have the problems of changing the device many times every day. In addition, in certain patients dexterity is deficient or limited. In such patient an indwelling female catheter is preferable. Several new devices have recently appeared in the marketplace. The first is marketed by Influence of San Francisco, Calif., while the other female device is marketed by UroQuest Medical Corporation of Sale Lake City, Utah. In both of these devices a metal valve is used. These two catheters must be inserted by the physician, or highly skilled nurse. In addition, the valve is activated by a magnetic device that must be carried by the female patient at all times. Both of these devices are stiff, thus stretching the urethra. This will be uncomfortable for the patient, and may lead to a higher incidence of urinary tract infection. In addition, intercourse is difficult due to the stiffness of the external part of the incontinence device. Intercourse may even dislodge and push the device intraurethrally. This will be very painful, and the patient must report to the nearest hospital for an emergency retrieval of the device. In addition, none of these devices have a safety valve system. If the bladder pressure reaches a dangerously high level, these valves will not open automatically.

It is therefore desirable to have a device that will prevent leakage of the urine. It is also desirable to have a device that the patient can tolerate with minimal or no discomfort. It is also desirable to have an incontinence device with a safety valve that does not open with transient increased intra-abdominal pressure as in coughing, straining, or sneezing, but will open in a continuous high bladder pressure condition. It is also desirable that the device will offer the female patient a normal life including exercise, intercourse, pregnancy and delivery without the smell of urine, or external pads.

The device should have an external padding large enough to prevent the migration into the urethra during strenuous activity, including sexual intercourse. The device should be easily introduced by any nurse, and by the patient after receiving instructions. The device should have a simple valve system that does not need a special tool or device to activate such valve. The valve should also be a safe valve. Safe valves will open spontaneously when the pressure in the bladder reaches a persistently dangerous high level.

The female urethra is always in a state of collapse except during micturition. Continuously stretching the urethra is painful, and can irritate the urethra producing urethritis or urinary tract infection. Therefore the device should be soft, and in a semi-collapsed state. When the valve is open to drain the urine in the bladder, the soft semi-collapsed catheter will stretch slightly to accommodate the flow of urine, thus duplicating the physiological status in the human urethra. A safety valve is used to ensure that a continuously high bladder pressure will not damage the kidneys and produce renal failure.

SUMMARY OF THE INVENTION

Accordingly, it is therefore an object of the present invention to provide a soft semi-collapsed catheter that is completely concealed by the incontinent female patient.

It is another object of the present invention to provide a hollow tube that drains the bladder by a mechanism activated by the female patient.

It is a further object of the present invention to have a catheter easily introduced into the bladder by the patient, nurse, or a doctor without the need for a special introducer.

It is still a further object of the present invention to provide a simple way to keep the catheter indwelling and could be removed by the female patient at any time she wishes to do so without the use of extra devices or tools.

It is a further object of the present invention to provide methods to minimize or prevent the migration of the device into the bladder.

It is yet a further object of the present invention to provide a simple and safe valve system, thus avoiding damage of the kidneys by a dangerously elevated bladder pressure.

These and other objects and advantages of the present invention will be more readily apparent in the description which follows.

DETAILED DESCRIPTION OF THE PREFERRED EMBODIMENTS

Figure 1:
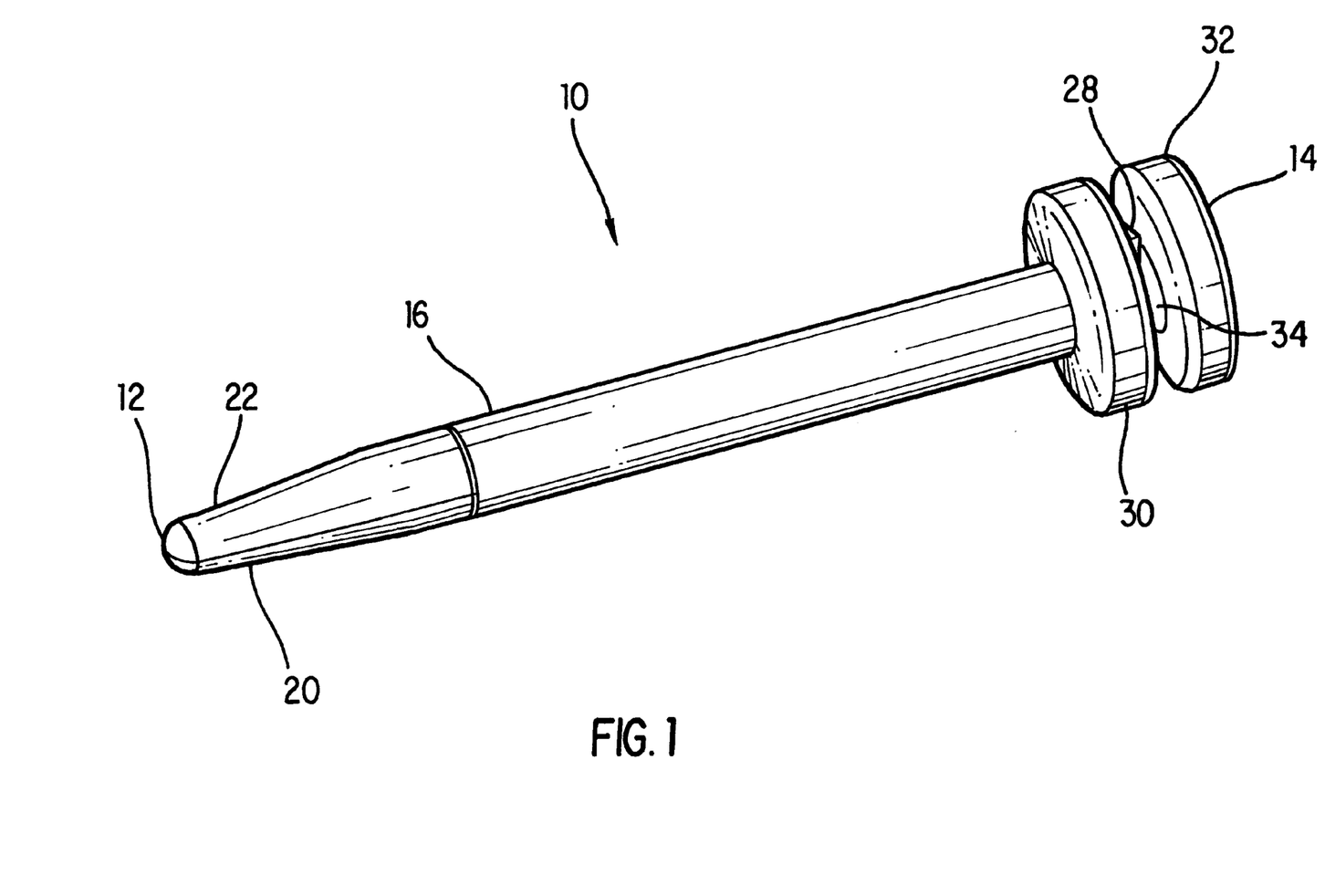
FIG. 1 is a perspective view of the female incontinence device of the present invention shown in its uninstalled state.

Referring now to FIG. 1, there is shown a female incontinence catheter, generally designated at 10, constructed according to the present invention. Catheter 10, which is shown in this figure in the uninstalled position prior to insertion into the bladder, is preferably constructed from a soft semi-collapsed hollow tube composed of a biocompatible material such as silicone rubber, and consists of a proximal section 12 and a distal section 14. Proximal section 12, which is inserted through the urethra in the bladder when installed within the patient, consists of tubular body portion 16 having an internal channel 18 (FIG. 2) and terminating at its proximal end in a pair of bifurcated members 20 and 22, which members are in apposition when catheter 10 is in the uninstalled position, as shown in FIG. 1. Body portion 16 also contains a pair of parallel channels 24, 26 along its length, and an aperture 28 which connects channel 18 to the exterior of catheter 10 (see FIGS. 5 and 6).

Figure 3:
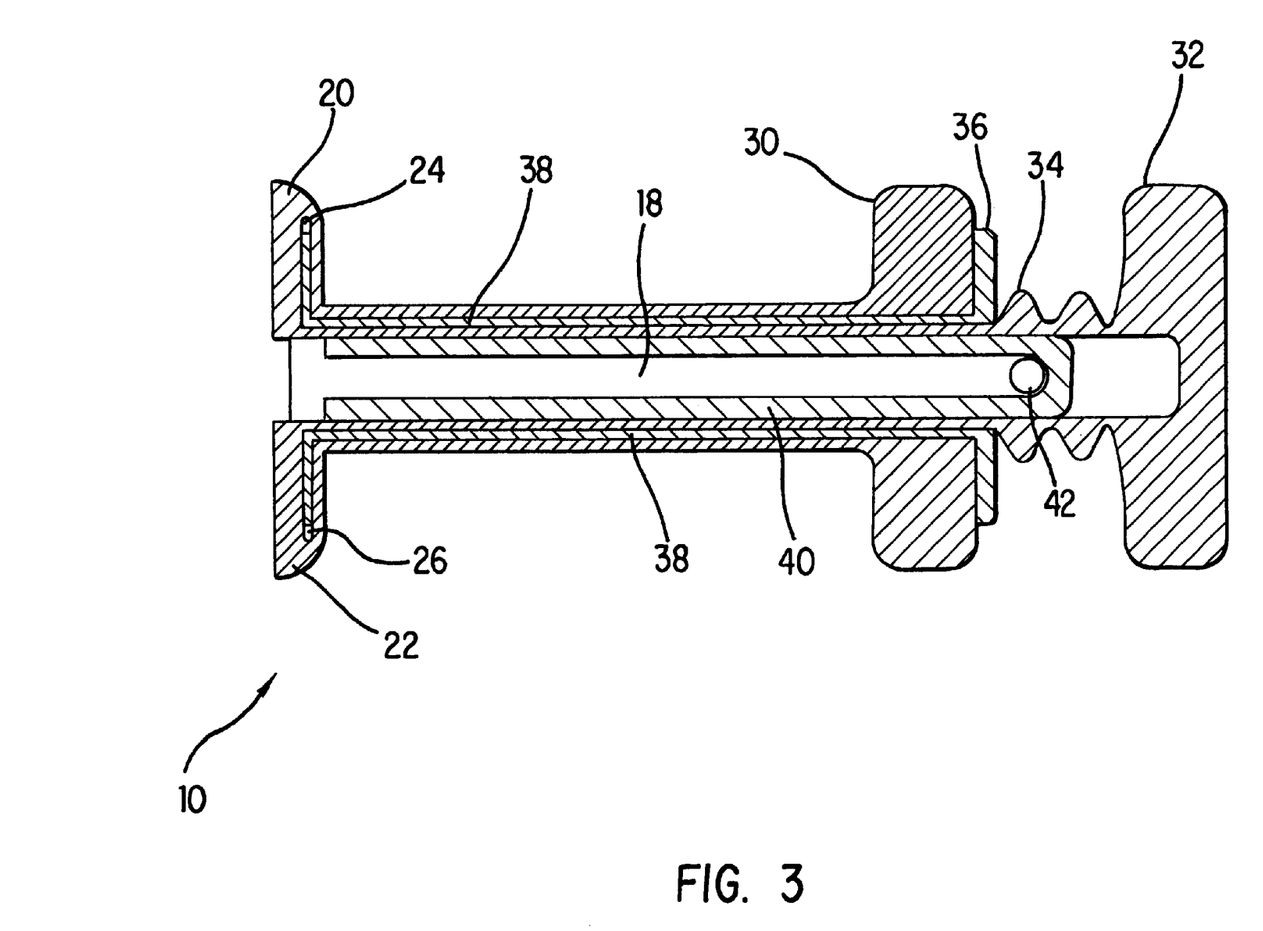
FIG. 3 is a cross-sectional view of the device shown in FIG. 2 with the self-retaining mechanism activated and the valve mechanism in the open position.
Figure 5:
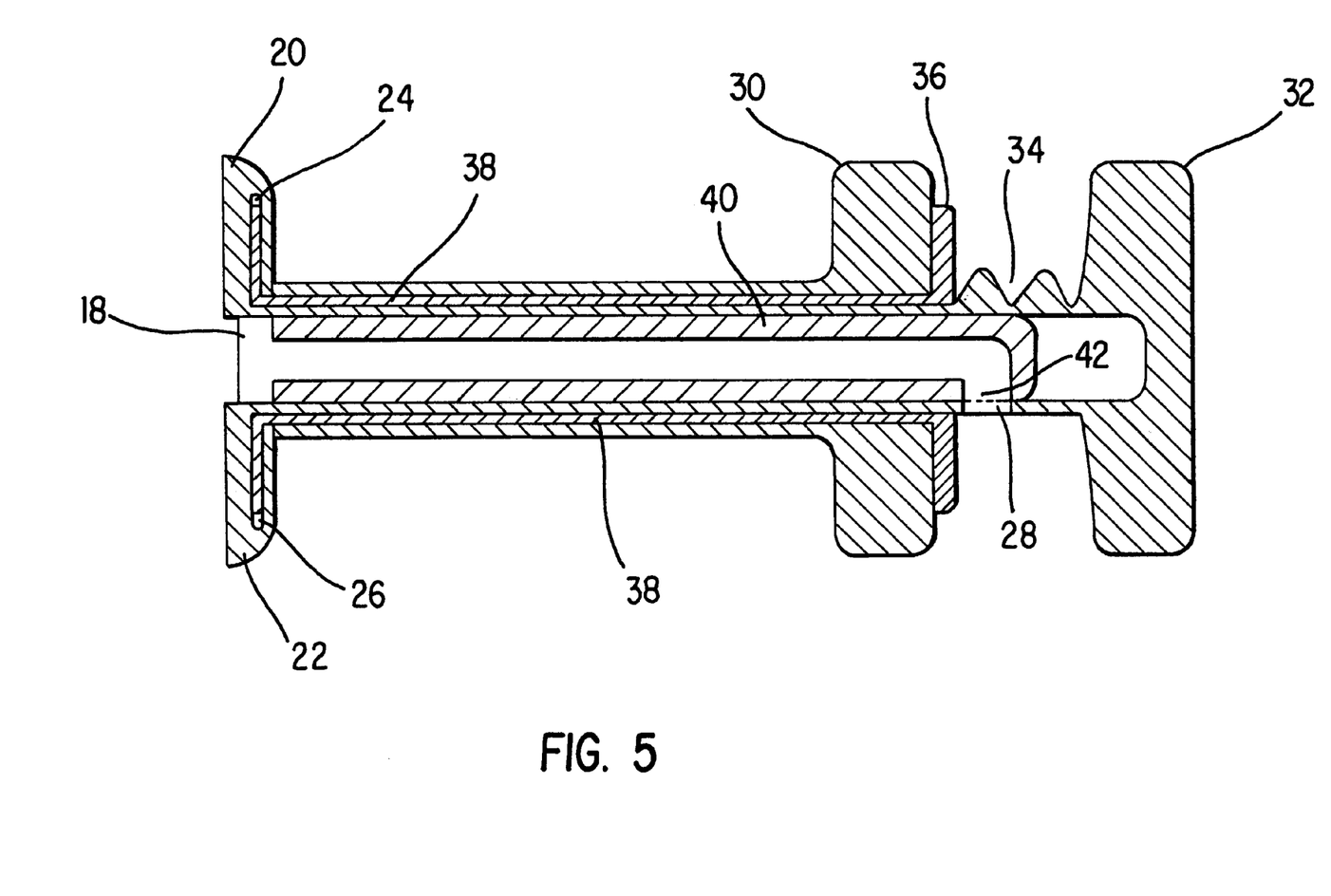
FIG. 5 is a cross-sectional side view of the device as shown in FIG. 3.
Figure 6:
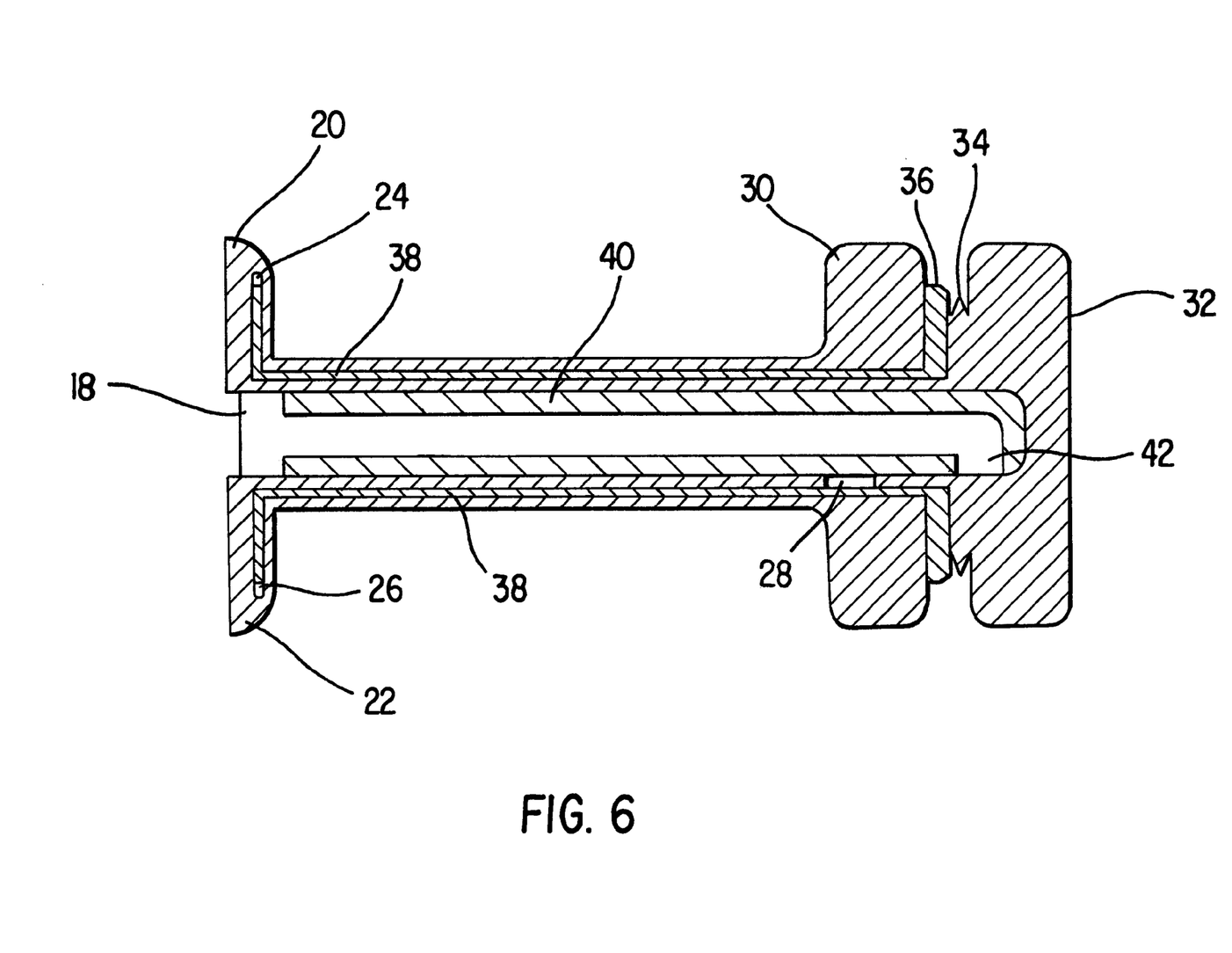
FIG. 6 is a cross-sectional side view of the device as shown in FIG. 4.

Distal section 14 of catheter 10 is provided with a pair of donut-shaped stops 30, 32 which are separated by an accordion-like spring section 34. In the normal at rest position of catheter 10, stops 30 and 32 are biased toward each other by spring section 34, as can be seen in FIGS. 3 and 5. Also located on section 14 of catheter 10 is an actuating mechanism 36 which consists of a pair of plastic rods 38 which are located within a pair of corresponding channels 24, 26 of body portion 16. Finally, an inner valve section 40 is affixed within channel 18 of catheter 10 and contains an aperture 42 which is aligned with aperture 28 of body portion 16 when stop 32 is shifted to its actuated position away from stop 30 against the tension force of spring section 34.

Proximal section 12 of catheter 10 also contains a pair of memory areas 44 located near bifurcated members 20, 22, while each of plastic rods 38 contain a corresponding memory area 46.

Having described the elements of the device of the present invention, the installation and operation of this embodiment of catheter 10 will now be described. Referring again to FIGS. 1 and 2, catheter 10 is lubricated and positioned by a healthcare professional or the patient by inserting proximal section 12 into the urethra until distal section 14 extends approximately one inch outside the urethral opening. Urine will begin to flow from distal section 14 through aligned apertures 28 and 42 of body portion 16 and valve section 40 respectively. The leakage indicates that proximal section 12 is correctly positioned within the urinary bladder.

Figure 2:
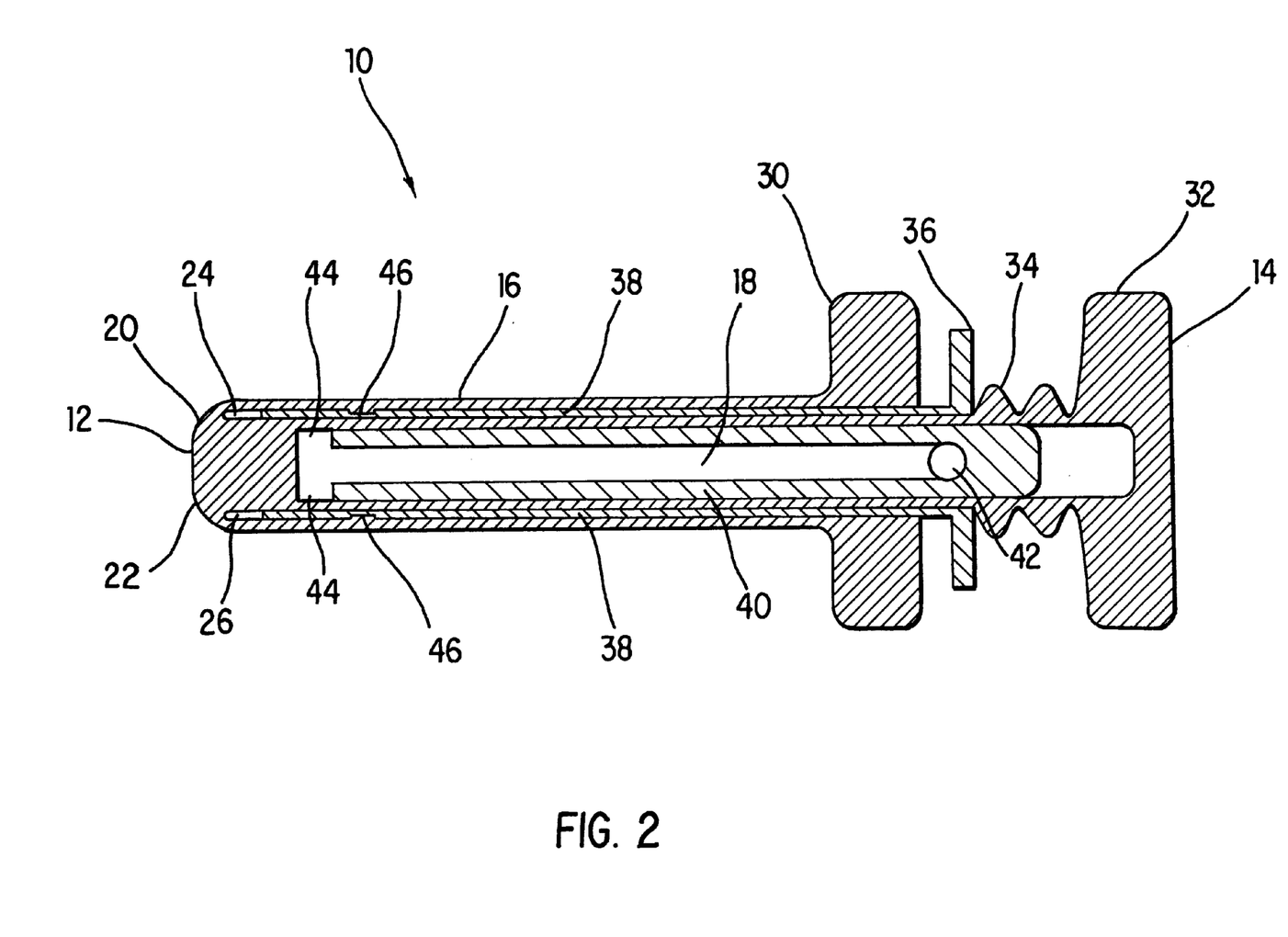
FIG. 2 is a cross-sectional elevational view of the female incontinence device of the present invention with the self-retaining mechanism inactivated and the valve mechanism in the open position.

After catheter 10 is positioned correctly, actuating mechanism 36 is shifted toward stop 30, causing rods 38 to shift within channels 24 and 26 of body portion toward the proximal end of catheter 10. The movement of rods 38 will bring memory areas 44 and 46 in opposition, forcing apart bifurcated members 20 and 22, as can be closely seen in FIG. 3. Catheter 10 is now in position as an indwelling device. Alternatively, catheter 10 can be designed such that rods 38 are tensioned in a way that bifurcated members 20 and 22 are normally positioned as shown in FIG. 3. When catheter 10 is removed from the package for installation into the bladder, a dissolvable sheath is positioned around members 20 and 22, holding them in the closed position as shown in FIG. 2. Upon insertion into the bladder, the sheath dissolves, allowing members 20 and 22 to spring open and secure catheter 10 in position within the bladder.

Figure 4:
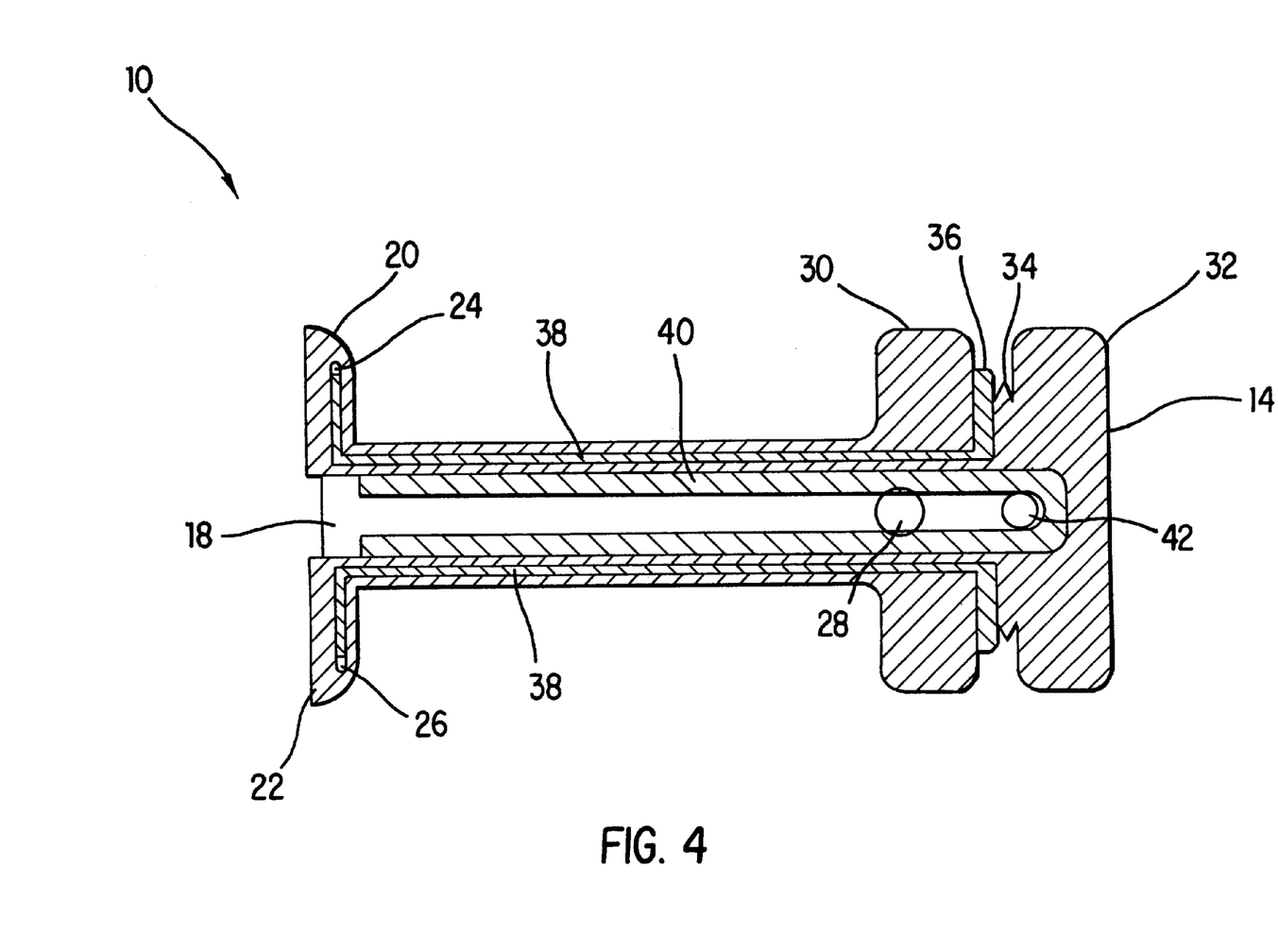
FIG. 4 is a cross-sectional view of the device shown in FIG. 2 with the self-retaining mechanism activated and the valve mechanism in the closed position.

Next, stops 30 and 32 are approximated by shifting stop 32 in the proximal direction, forcing spring section 34 to its closed position, as can be most clearly seen in FIG. 4. Note that apertures 28 and 42 are not aligned, thus achieving continence in the patient.

Stops 30 and 32, which measure approximately 55–60 French in diameter, act to prevent proximal migration of catheter 10 into the bladder. In addition, stops 30 and 32 act as a cushion during sexual intercourse.

When the patient desires to empty her bladder, she will insinuate her fingers between stops 30 and 32 of catheter 10. This action separates stops 30 and 32 against the tension force of spring section 34. Separation of stops 30 and 32 causes aperture 28 of tubular section 16 to align with aperture 42 of fixed section 40, thus allowing urine to escape from the bladder through channel 18, as can be clearly seen in FIG. 5. The action of spring section 34, which biases stop 32 toward fixed stop 30, will eventually shift stop 32 back to its at rest position proximate stop 30 in 40 to 60 seconds. After this time period has expired, apertures 28 and 42 are no longer aligned, and continence is again achieved. However, during this 40 to 60 second time period, the bladder of the patient would have been completely emptied.

Catheter 10 can be removed from the bladder and urethra of the patient by shifting activating mechanism 36 away from stop 30, causing members 20 and 22 to return to the unactivated state in apposition to each other, allowing catheter 10 to be easily withdrawn.

In rare cases when the patient does not feel bladder distention, as in progressive multiple sclerosis, or in an inappropriate indication for such a device, the valve system of the present invention will automatically open by the mere persistently high pressure of the distended bladder. This continuous high bladder pressure will push the distal moving part of catheter 10 to overcome the recoil force of accordion-like spring section 34 in such a way that apertures 28 and 42 will align, allowing the urine to start flowing from the bladder through channel 18, and thus automatically emptying the bladder and preventing any damaging back pressure to the kidneys from the very high bladder pressure.

FIGS. 7–10 serve to illustrate an alternative embodiment of the present invention. It will be appreciated that, in this embodiment, similar parts are given the same numerals as the first embodiment.

Figure 7:
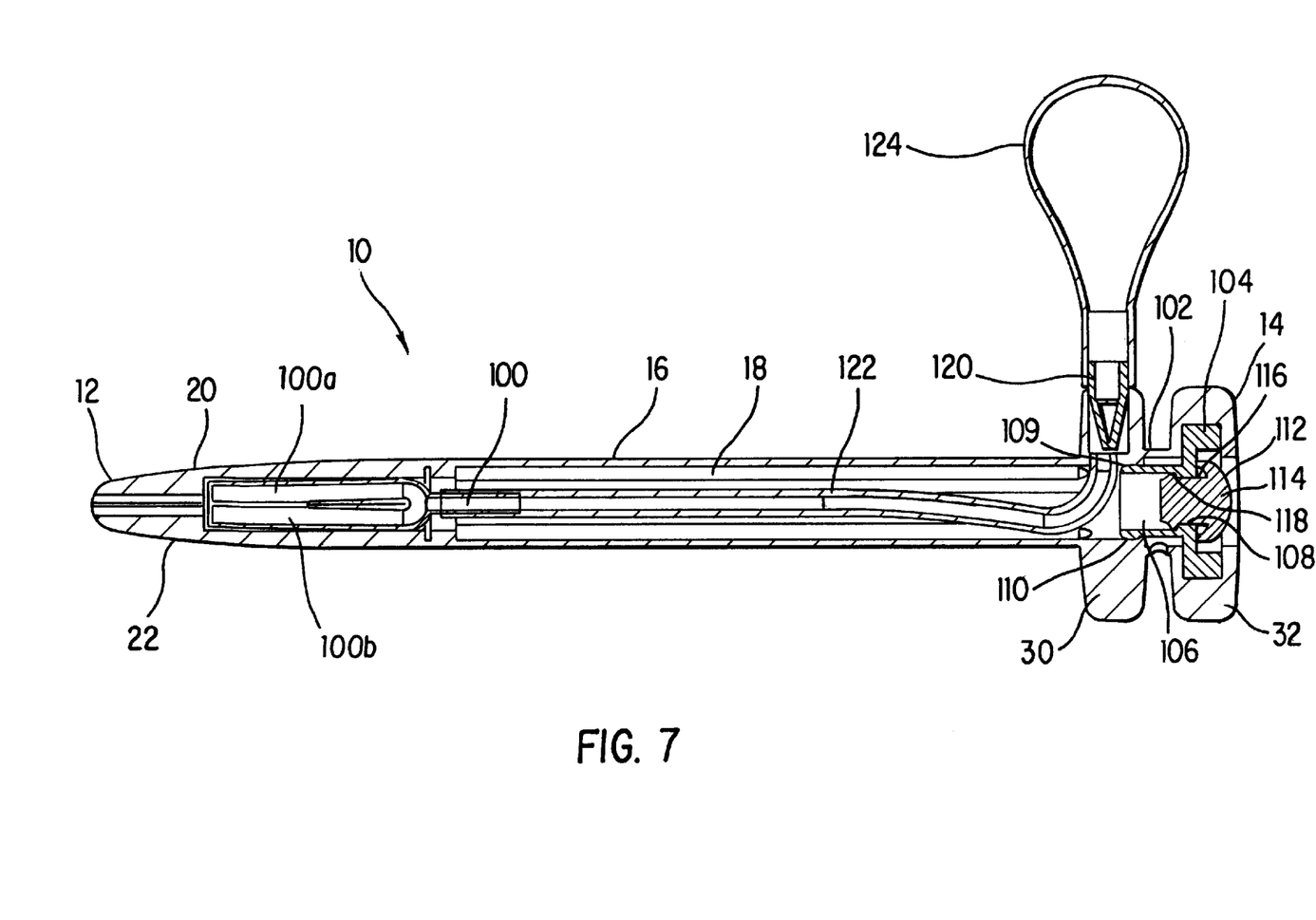
FIG. 7 shows, in cross section, an alternative embodiment of the female incontinence device of the present invention in its uninstalled state.
Figure 8:
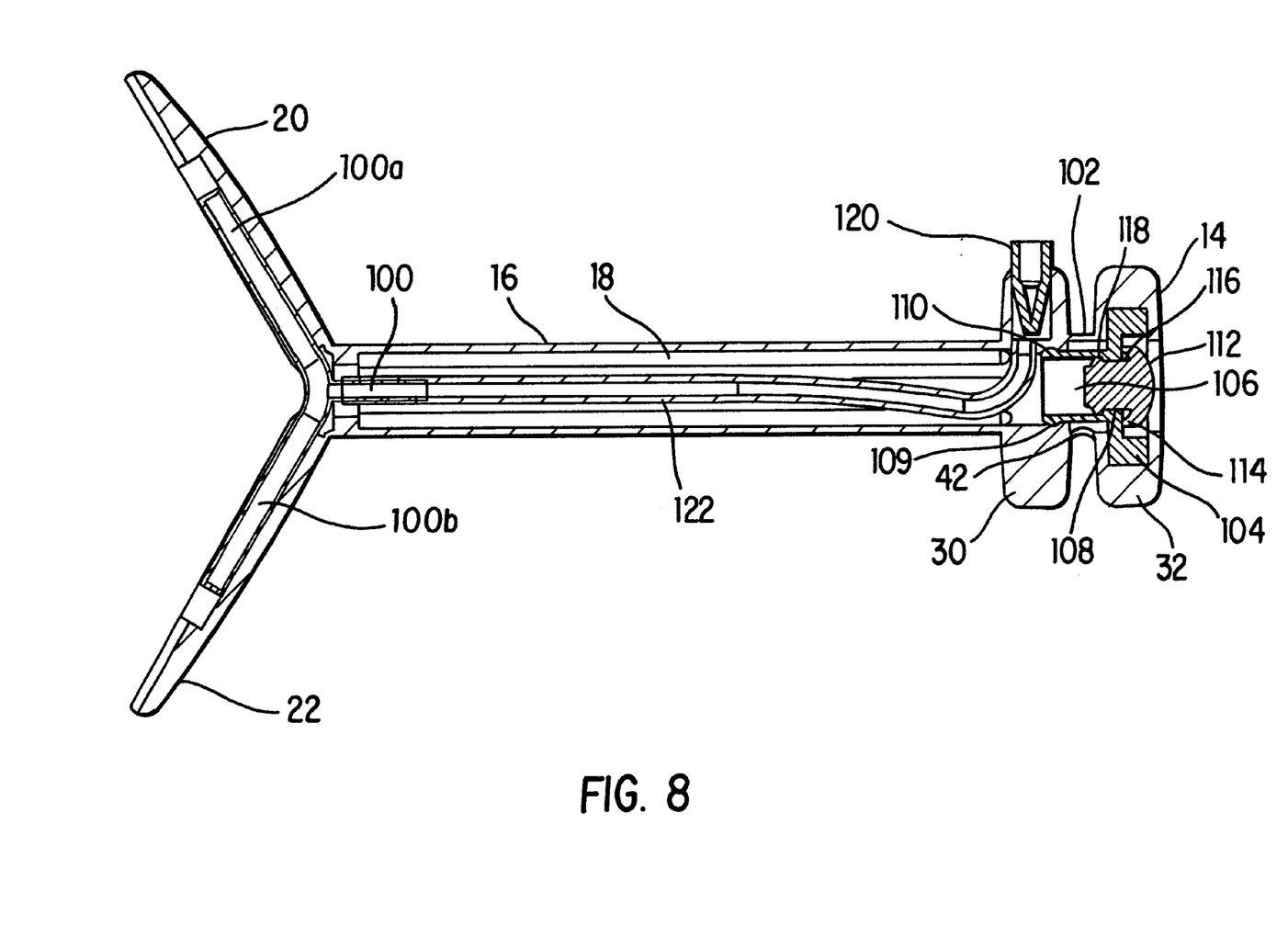
FIG. 8 is a cross-sectional view of the device of FIG. 7 with the self-retaining mechanism activated.

Referring now to FIG. 7, catheter 10 consists of a proximal section 12 and a distal section 14 having a tubular body portion 16, preferably constructed from molded silicone, which contains an internal channel 18 and terminates at its proximal end in a pair of bifurcated members 20 and 22, which members are in apposition when catheter 10 is in its uninstalled position. Also located within channel 18 is a tube 100 which terminates near the proximal section 12 of catheter 10 in a pair of bifurcated sections 100a and 100b which correspond to members 20 and 22. In this embodiment, tube section 100a is affixed within member 20, while tube section 100b is affixed within member 22.

Distal section 14 of catheter 10 is provided with a pair of donut-shaped stops 30, 32 which are separated by a flexible section 102. Section 102 contains an aperture 28 which allows internal channel 18 to communicate with the exterior of catheter 10. In the present embodiment, catheter body 16, members 20 and 22, stops 30 and 32, and section 102 are molded as a single piece, preferably from silicone. Located within channel 18 between stops 30 and 32 is a valve plug 104. Valve 104 consists of a cylindrical plug constructed from polyethylene having an internal channel 106 which passes through valve 104, and also contains a radial flange 108 within channel 106. The proximal end 109 of valve 104 is sized such that it contacts an internal surface 110 of stop 30.

Valve 104 is fixedly mounted within stop 32 of catheter 10. In operation, as stop 32 is shifted away from stop 30, flange 109 of valve 104 no longer contacts surface 110 of stop 30, and thus internal channel 18 of catheter 10 communicates with the exterior of catheter 10 via aperture 28 in section 102.

In addition, a check valve 112 is positioned within valve plug 104. Check valve 112 consists of an enlarged umbrella or mushroom shaped distal end 114, a cylindrical central portion 116, and a proximal flange 118. In the assembly of catheter 10, check valve 112 is introduced into channel 106 of valve plug 104 such that central portion 116 is positioned within radial flange 108, and check valve 112 is held in place by enlarged end 114 and flange 118 on opposing sides of flange 108.

Finally, a one-way duckbill check valve 120 is located through the outer surface of stop 30, and is coupled to tube 100 within internal channel of catheter 10 via a silicone hose section 122. Check valve 120 is designed to receive a fluid-filled bulb 124 capable of injecting fluid through hose 122 into tube 100 for the purpose of inflating tube 100 to separate members 20 and 22 after insertion of catheter 10 into the bladder of a patient.

Having described the elements of this embodiment, its installation and operation will now be described. Referring again to FIG. 7, a fluid-filled bulb 124 is affixed to check valve 120 within stop 30 of catheter 10. The fluid within bulb 124 is preferably a saline solution, but may also be air or any fluid which can be safely introduced into the body. Proximal end 12 is then inserted through the urethra into the bladder, as previously described. After catheter 10 has been correctly positioned, bulb 124 is squeezed, forcing fluid through check valve 120 and hose 122, into tube 100. The pressure within tube 100 causes sections 100a and 100b to separate, as can be clearly seen in FIG. 8. Flared members 20 and 22 now act to hold catheter 10 in its proper position within the bladder. Bulb 124 may now be removed, as one-way check valve 120 keeps the fluid within catheter 10.

Figure 9:
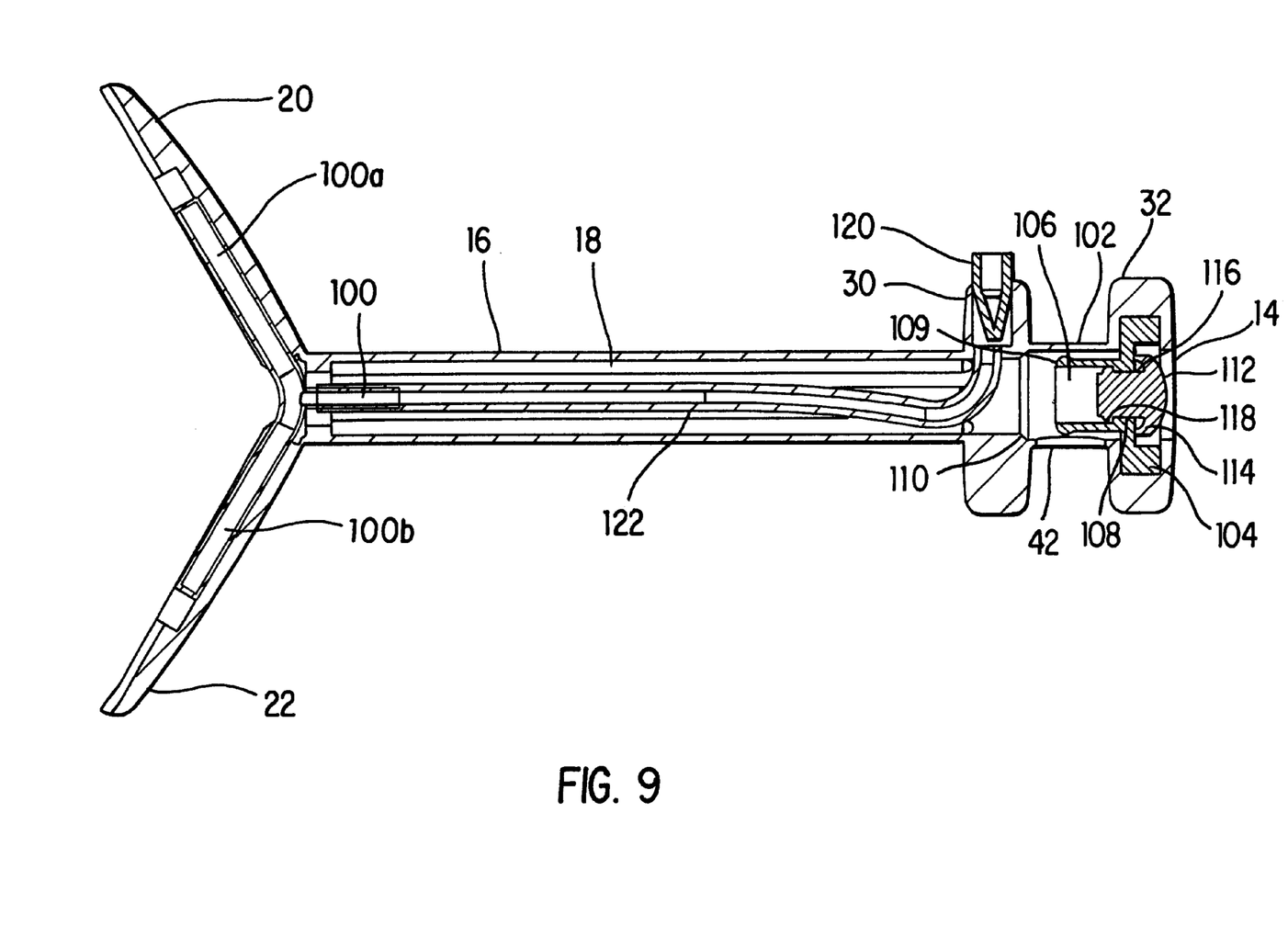
FIG. 9 is a cross-sectional view of the device of FIG. 7 with the self-retaining mechanism activated and the valve mechanism in the open position.

FIG. 9 shows catheter 10 in the installed position with the draining apparatus activated. To drain the bladder, the patient insinuates her fingers between stops 30 and 32, and shifts stop 32 downwardly against the force of flexible section 102 approximately 3 to 6 mm. This action causes flange 108 of valve 104 to unseat from surface 110 of stop 30, thus allowing urine to flow from the bladder from internal channel 18 through aperture 28 out of catheter 10. Urine will continue to flow as long as the patient retains stop 32 in its extended position; when stop 32 is released, flexible section 102 retracts stop 32 to reseat valve 104 against surface 110 to stop 30.

In those situations in which the bladder pressure rises to a dangerously high condition, check valve 112 will be forced out of its position within radial flange 108 by the pressure exerted within catheter 10 by the urine, thus opening internal channel 18 to the exterior of catheter 10. Preferably, valve 112 is designed to fail when the bladder pressure exceed 150–200 cm $H_2O$.

Figure 10:
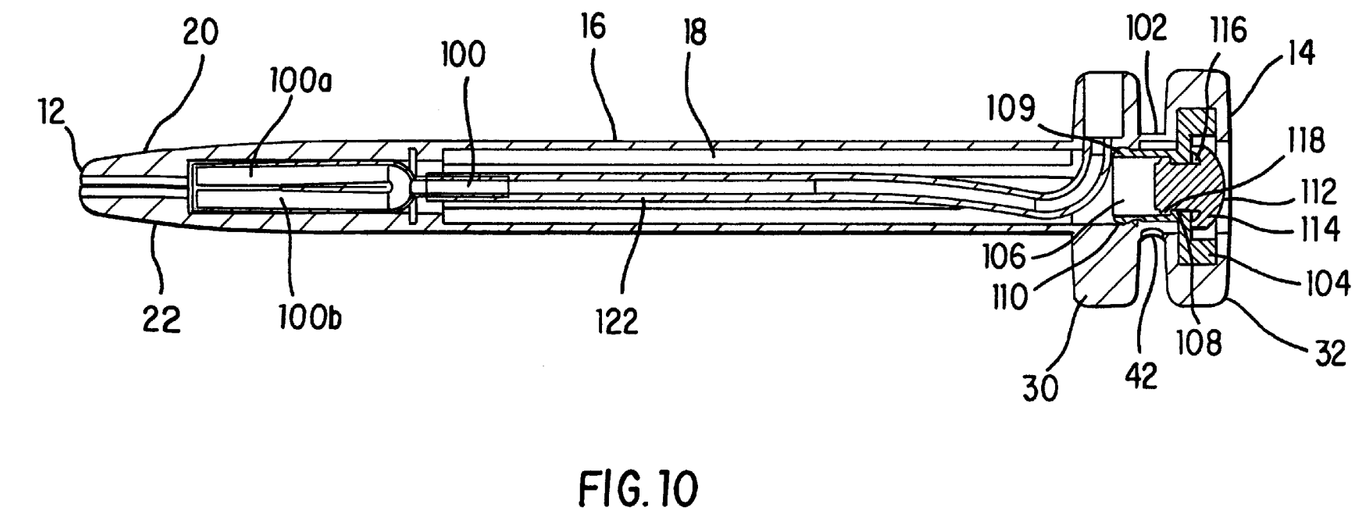
FIG. 10 is a cross-sectional view of the device of FIG. 7 in its deactivated state for removal from the urethra.

When it is desired that catheter 10 be removed, duckbill check valve 120 is removed from the outer flange of stop 30, allowing the fluid within tube 100 to drain to the exterior of catheter 10, relieving fluid pressure in sections 100a and 100b and allowing members 20 and 22 to return to the position shown in FIG. 7. Catheter 10 car now be easily withdrawn from the bladder and urethra.

While the present invention has been shown and described in terms of a preferred embodiment thereof, it will be understood that this invention is not limited to this particular embodiment and that many changes and modifications may be made without departing from the true spirit and scope of the invention as defined in the appended claims. In addition, as used herein and in the claims, such words as "distal", "proximal", "top", "bottom", "side", and the like are used in conjunction with the drawings for purposes of clarity, and it will be appreciated that they do not limit the device to a particular orientation.

What is claimed is:

1. An apparatus adapted for controlling female urinary incontinence comprising:

(a) a substantially tubular body portion adapted for removable insert into the urinary tract of a female user, said body portion having a longitudinally extended internal channel defined between proximal and distal ends thereof;

(b) a retention portion coupled to said body portion adjacent said proximal end thereof, said retention portion being selectively reconfigurable between installed and uninstalled configurations;

(c) a manual activation portion coupled to said body portion adjacent said distal end thereof, said manual activation portion including: a pair of radially extended stops longitudinally displaceable at least one relative to the other between open and closed positions, and an integrally formed spring section disposed therebetween for resiliently biasing said displaceable stop toward said closed position, said body portion internal channel being opened for drainage of the user's urine therefrom upon said displaceable stop being disposed in said open position; and, (d) a control mechanism formed in said manual activation portion for automatically opening said body portion internal channel for drainage of the user's urine therefrom responsive to a triggering condition wherein an internal pressure parameter within the user's urinary tract exceeding a predetermined value.

2. The apparatus as recited in claim 1 wherein said retention portion includes a plurality of angularly displaceable retention members, said retention members being disposed in substantially flush contact one with the other in said uninstalled configuration and separated one from the other in said installed configuration to retentively engage respective portions of the user's bladder wall.

3. The apparatus as recited in claim 1 wherein said control mechanism includes said spring section having a contractive accordion-like configuration, said spring section being longitudinally extendable responsive to the occurrence of said triggering condition for displacing said displaceable stop to said open position.

4. The apparatus as recited in claim 1 wherein said control mechanism includes a deformable check valve coupled to said displaceable stop, said check valve being resiliently deflectable relative to said displaceable stop responsive to the occurrence of said triggering condition to open said body portion internal channel for drainage of the user's urine therefrom.

5. The apparatus as recited in claim 2 further comprising an actuation mechanism coupled to said retention members and extending substantially between said proximal and distal ends of said body portion, said actuation mechanism being longitudinally displaceable relative to said body portion to reversibly actuate said angular displacement of said retention members between said installed and uninstalled configurations thereof.

6. The apparatus as recited in claim 2 further comprising a fluid pressure-driven actuation mechanism coupled to said retention members and extending substantially between said proximal and distal ends of said body portion, said actuation mechanism being operable to reversibly actuate said angular displacement of said retention members between said installed and uninstalled configurations thereof.

7. An apparatus adapted for controlling female urinary incontinence comprising:
  (a) a substantially tubular body portion adapted for removable insert into the urinary tract of a female user, said body portion having a longitudinally extended internal channel defined between proximal and distal ends thereof, said body portion having formed therein a first opening communicating with said internal channel;
  (b) a retention portion coupled to said body portion adjacent said proximal end thereof, said retention portion being selectively reconfigurable between installed and uninstalled configurations;
  (c) an elongate inner valve section coaxially disposed within said body portion internal channel for partitioning at least a portion of said internal channel, said inner valve section having formed therein a second opening communicating with said partitioned portion of said internal channel; and,
  (d) a manual activation portion coupled to said body portion adjacent said distal end thereof, said manual activation portion including:
    (1) a pair of radially extended stops longitudinally displaceable at least one relative to the other between open and closed positions, said first and second openings being substantially aligned to open said partitioned portion of said body portion internal channel for drainage of the user's urine therefrom upon said displaceable stop being disposed in said open position; and,
    (2) a spring section integrally formed with and disposed between said stops for resiliently biasing said displaceable stop toward said closed position, said spring section being automatically reconfigurable against said bias thereof to displace said displaceable stop to said open position responsive to a triggering condition wherein an internal pressure parameter within the user's urinary tract exceeds a predetermined value.

8. The apparatus as recited in claim 7 wherein said retention portion includes a plurality of angularly displaceable retention members, said retention members being disposed in substantially flush contact one with the other in said uninstalled configuration and separated one from the other in said installed configuration to retentively engage respective portions of the user's bladder wall.

9. The apparatus as recited in claim 8 further comprising an actuation mechanism coupled to said retention members and extending substantially between said proximal and distal ends of said body portion, said actuation mechanism being longitudinally displaceable relative to said body portion to reversibly actuate said angular displacement of said retention members between said installed and uninstalled configurations thereof.

10. The apparatus as recited in claim 7 wherein said spring section is formed having an accordion-like configuration, said spring section being longitudinally extendable responsive to the occurrence of said triggering condition for displacing said displaceable stop to said open position.

11. The apparatus as recited in claim 10 wherein said spring section is adapted to retract said displaceable stop to said closed position from said open position thereof within a retraction period between approximately 40 to 60 seconds.

12. The apparatus as recited in claim 7 wherein said predetermined value of said triggering condition ranges approximately between 150 and 200 cm $H_2O$.

13. The apparatus as recited in claim 7 wherein said body portion is formed of a composition containing a silicone material.

14. An apparatus adapted for controlling female urinary incontinence comprising:
  (a) a substantially tubular body portion adapted for removable insert into the urinary tract of a female user, said body portion having a longitudinally extended internal channel defined between proximal and distal ends thereof;
  (b) a retention portion coupled to said body portion adjacent said proximal end thereof, said retention portion being selectively reconfigurable between installed and uninstalled configurations;
  (c) a manual activation portion coupled to said body portion adjacent said distal end thereof, said manual activation portion including: a radially extended first stop, a radially extended second stop longitudinally displaceable relative to said first stop between open and closed positions, and a spring section integrally formed between said first and second stops for resiliently biasing said second stop toward said closed position, said second stop having a valve member engaging said first stop in substantially sealed manner when disposed in said closed position to close said internal channel against drainage of the user's urine therefrom; and,
  (d) a deformable check valve coupled to said second stop, said check valve being resiliently deflectable relative to said second stop to automatically open said body portion internal channel for drainage of the user's urine therefrom responsive to a triggering condition wherein an internal pressure parameter within the user's urinary tract exceeds a predetermined value.

15. The apparatus as recited in claim 14 wherein said retention portion includes a plurality of angularly displaceable retention members, said retention members being disposed in substantially flush contact one with the other in said uninstalled configuration and separated one from the other in said installed configuration to retentively engage respective portions of the user's bladder wall.

16. The apparatus as recited in claim 15 further comprising a fluid pressure-driven actuation mechanism coupled to said retention members and extending substantially between said proximal and distal ends of said body portion, said actuation mechanism being operable to reversibly actuate said angular displacement of said retention members between said installed and uninstalled configurations thereof.

17. The apparatus as recited in claim 16 wherein said actuation mechanism includes a fluid conduit extending along said body portion and a fluid source operably coupled thereto, said retention members being angularly displaceable responsive to sufficient injection of a fluid from said fluid source into said fluid conduit.

18. The apparatus as recited in claim 17 wherein said actuation mechanism further includes a one-way fluid check valve disposed between said fluid source and said fluid conduit for said injection of said fluid therethrough, said fluid source being removable upon said fluid injection.

19. The apparatus as recited in claim 14 wherein said predetermined value of said triggering condition equals approximately 150 cm $H_2O$.

20. The apparatus as recited in claim 14 wherein said body portion is formed of a composition containing a silicone material.

* * * * *